United States Patent [19]

Kopp et al.

[11] Patent Number: 4,746,436

[45] Date of Patent: May 24, 1988

[54] MEMBRANE PLASMAPHERESIS APPARATUS AND PROCESS WHICH UTILIZE A FLEXIBLE WALL TO VARIABLY RESTRICT THE FLOW OF PLASMA FILTRATE AND THEREBY STABILIZE TRANSMEMBRANE PRESSURE

[75] Inventors: Clinton V. Kopp; James Hitchcock, both of Barrington, Ill.

[73] Assignee: Baxter Travenol Laboratories, Inc., Deerfield, Ill.

[21] Appl. No.: 942,062

[22] Filed: Dec. 15, 1986

Related U.S. Application Data

[63] Continuation of Ser. No. 542,565, Oct. 19, 1983, abandoned, which is a continuation of Ser. No. 277,428, Jun. 25, 1981, abandoned.

[51] Int. Cl.⁴ ............................................. B01D 13/00
[52] U.S. Cl. .................................. 210/637; 210/109; 210/137; 210/321.65; 210/321.89; 210/651; 210/741
[58] Field of Search ............... 210/637, 650, 651, 741, 210/87, 90, 109, 137, 321, 433, 321.65, 321.84, 321.89; 542/565

[56] References Cited

U.S. PATENT DOCUMENTS

| | | |
|---|---|---|
| 1,524,217 | 1/1925 | Small . |
| 2,296,833 | 9/1942 | Boynton . |
| 2,416,161 | 2/1947 | Deck .................................. 158/27.4 |
| 2,572,175 | 10/1951 | McPherson ......................... 251/61.1 |
| 2,736,332 | 2/1956 | Simmons ................................. 137/87 |
| 2,837,102 | 6/1958 | Bauer et al. ............................. 137/7 |
| 2,850,038 | 9/1958 | Shabaker .......................... 137/505.13 |
| 2,857,803 | 10/1958 | Reinecke et al. ......................... 88/14 |
| 2,905,431 | 9/1959 | Gilbert .............................. 251/61.1 |
| 2,943,643 | 7/1960 | Pinter et al. .......................... 138/46 |
| 2,992,652 | 7/1961 | Fellberg ........................... 251/331 X |
| 3,052,064 | 9/1962 | Kaeser ................................... 49/21 |
| 3,057,376 | 10/1962 | Agutter et al. ........................ 137/594 |
| 3,083,943 | 4/1963 | Stewart et al. ......................... 251/61 |
| 3,150,674 | 9/1964 | Connaught ............................. 137/82 |
| 3,170,477 | 2/1965 | Scott, Jr. et al. ..................... 137/183 |
| 3,319,926 | 5/1967 | Boger ................................... 251/61 |
| 3,465,752 | 9/1969 | Brychta et al. ..................... 128/145.8 |
| 3,490,479 | 1/1970 | Mott et al. .............................. 137/82 |
| 3,693,611 | 9/1972 | Ploss .................................. 137/87 X |
| 3,705,100 | 12/1972 | Blatt et al. ....................... 210/456 X |

(List continued on next page.)

FOREIGN PATENT DOCUMENTS

| | | |
|---|---|---|
| 1300388 | 7/1969 | Fed. Rep. of Germany . |
| 1775724 | 9/1971 | Fed. Rep. of Germany . |
| WO79/01121 | 12/1979 | PCT Int'l Appl. . |
| 8002377 | 11/1980 | PCT Int'l Appl. . |
| 796476 | 1/1981 | U.S.S.R. . |

OTHER PUBLICATIONS

Green et al., "Measurement of the Transmittance Coefficient Spectrum of Cuprophan and RP69 Membranes: Ultrafiltration", *Am. Soc. for Artificial Internal Organs*, vol. XXII, 1976, pp. 627–636.

Solomon et al., "Continuous Flow Membrane Filtration of Plasma from Whole Blood," vol. XXIV, Trans, Amer. Soc. Artif. Int. Organs, (1978), pp. 21 through 26.

Primary Examiner—Richard V. Fisher
Assistant Examiner—W. Gary Jones
Attorney, Agent, or Firm—Paul C. Flattery; Bradford R. L. Price

[57] ABSTRACT

A membrane plasmapheresis system introduces a flow of whole blood subject to a predetermined inlet pressure into a fluid path across a membrane which is suited for filtering the plasma from the whole blood and across which a predetermined pressure drop occurs. The plasma-poor blood is conducted from the membrane subject to a determinable plasma-poor blood pressure. Likewise, plasma filtrate is conducted from the membrane subject to a determinable plasma-filtrate pressure. The conduction of plasma filtrate is metered in response to the existent plasma-poor blood pressure to achieve and thereafter maintain substantial equilibrium between the plasma-poor blood pressure and the plasma filtrate pressure. A substantially constant transmembrane pressure can thereby be maintained at a level below which hemolysis occurs.

20 Claims, 3 Drawing Sheets

U.S. PATENT DOCUMENTS

| | | | |
|---|---|---|---|
| 3,779,267 | 12/1973 | Cowan | 137/111 |
| 3,791,397 | 2/1974 | Janu | 137/82 |
| 3,795,318 | 3/1974 | Crane et al. | 210/321 |
| 3,807,426 | 4/1974 | Henes | 137/100 |
| 3,853,147 | 12/1974 | Cibulka | 138/30 |
| 3,856,046 | 12/1974 | Brown et al. | 137/625.28 |
| 3,917,162 | 11/1975 | Trotter et al. | 236/28 |
| 3,918,677 | 11/1975 | Cowan | 251/61.1 |
| 3,929,148 | 12/1975 | Midy | 137/84 |
| 3,957,073 | 5/1976 | Barnum | 137/87 |
| 4,089,342 | 5/1978 | Stradella et al. | 137/102 |
| 4,113,614 | 9/1978 | Rollo et al. | 210/90 X |
| 4,142,523 | 3/1979 | Stegeman | 128/214 R |
| 4,178,938 | 12/1979 | Au | 128/207.15 |
| 4,181,245 | 1/1980 | Garrett et al. | 222/450 |
| 4,191,182 | 3/1980 | Popovich et al. | 128/214 |
| 4,212,742 | 7/1980 | Solomon et al. | 210/247 |
| 4,214,601 | 7/1980 | Sama | 137/102 |
| 4,274,452 | 6/1981 | Schmitt | 141/1 |
| 4,303,068 | 12/1981 | Zelman | 128/214 B |
| 4,304,260 | 12/1981 | Turner et al. | 137/613 |
| 4,315,520 | 2/1982 | Atkinson et al. | 137/82 |
| 4,321,939 | 3/1982 | Fenwick | 137/87 X |
| 4,412,553 | 11/1983 | Kopp et al. | 137/118 |
| 4,431,019 | 2/1984 | Kopp et al. | 137/87 |

MEMBRANE PLASMAPHERESIS APPARATUS AND PROCESS WHICH UTILIZE A FLEXIBLE WALL TO VARIABLY RESTRICT THE FLOW OF PLASMA FILTRATE AND THEREBY STABILIZE TRANSMEMBRANE PRESSURE

This is a continuation of application Ser. No. 542,565, filed on Oct. 19, 1983, which is a continuation of application Ser. No. 277,428, filed June 25, 1981, both now abandoned.

FIELD OF THE INVENTION

This invention generally relates to membrane plasmapheresis apparatus and processes.

DESCRIPTION OF THE PRIOR ART

During the process of membrane plasmapheresis, plasma is removed from whole blood by filtration through a microporous membrane. In order for plasma to pass through the membrane, a driving force is required. This force is known as the transmembrane pressure.

When the transmembrane pressure is at an operationally desirable level, the blood flows across the membrane with a sufficient velocity and sheer rate to cause only plasma to pass through the pores of the membrane for collection. However, should the transmembrane pressure rise above a certain critical level, the red cells can themselves be forced into the membrane pores and be hemolyzed.

Effecting the magnitude of the transmembrane pressure is the inlet pressure of the whole blood, as well as the resistance the whole blood encounters as it travels across the membrane. Also contributing to the magnitude of the transmembrane pressure is the resistance the plasma-poor blood encounters as it is being returned to the patient-donor through an associated transfusion set, phlebotomy needle, blood warmer and other ancillary apparatus located downstream of the membrane. The blood pressure of the individual patient-donor and movement of his or her arm during the course of the procedure also serve to increase this downstream resistance, which can and typically does fluctuate suddenly and randomly.

These sudden and random fluctuations in the resistance to the flow of plasma-poor blood can elevate the transmembrane pressure to a point where hemolysis occurs.

In the past, efforts to minimize the magnitude of the downstream resistance encountered during membrane plasmapheresis, and thus to stabilize the transmembrane pressure at operationally desirable levels, have included the use of a larger needle, which can, of course, contribute to patient discomfort; foregoing the use of ancillary equipment downstream of the membrane, even through operationally desirable; and continuously changing the elevation of the plasma filtrate collection container during the procedure. These efforts are, at best, stopgap measures and often run counter to the overall objectives of a comfortable and efficient membrane plasmapheresis operation.

Attention is also directed to Popovich et al., U.S. Pat. No. 4,191,182 issued Mar. 4, 1980. In the plasmapheresis procedure therein disclosed, the plasma filtrate is constantly recirculated over the filtering side of the membrane to stabilize the transmembrane pressure across the length of the membrane. However, such a procedure fails to address the problems associated with random and sudden pressure fluctuations occurring downstream of the membrane.

It is one of the principal objects of this invention to provide a membrane plasmapheresis system in which the transmembrane pressure is maintained at a stable and constant magnitude below the level at which hemolysis occurs.

It is another principal object of this invention to provide a membrane plasmapheresis system in which the magnitude of the transmembrane pressure is subject to the constant control of the operator and does not experience sudden and random fluctuations.

It is yet another principal object of this invention to provide a membrane plasmapheresis system which permits both the comfort of the patient-donor as well as the operational efficiency of the procedure itself to be maximized to the fullest extent possible.

SUMMARY OF THE INVENTION

To achieve these and other objects, the invention provides a membrane plasmapheresis process and apparatus in which a flow of whole blood is established at an operator-controlled inlet pressure across a membrane which has a pore size suited for filtering the plasma from whole blood and across which an operator-controlled pressure drop occurs. The plasma-poor blood is conducted from the membrane subject to a determinable plasma-poor blood pressure. The plasma filtrate is likewise conducted from the membrane subject to its own determinable pressure. The conduction of plasma filtrate is continuously metered in response to the then existent plasma-poor blood pressure to maintain substantial equilibrium between the pressure of the plasma filtrate and the pressure of the plasma-poor blood.

In the preferred embodiment, the membrane plasmapheresis process and apparatus equalize the downstream pressures of the plasma filtrate and plasma-poor blood without interrupting the conduction of either blood component from the membrane.

The invention thus provides a plasmapheresis process and apparatus having a constant and stable transmembrane pressure which is subject to control by the operator and which is uneffected by sudden and random fluctuations in the plasma-poor blood pressure downstream of the membrane. The invention also provides a process and apparatus in which an uninterrupted flow of plasma filtrate and plasma-poor blood occurs downstream of the module. At the same time, the invention permits the use of ancillary equipment downstream of the membrane to maximize the operational efficiency of the membrane plasmapheresis procedure, without the attendant fear of elevating the transmembrane pressure above a point where hemolysis can occur.

Other features and advantages of the invention will be pointed out in, or will be apparent from, the specification and claims, as will obvious modifications of the embodiments shown in the drawings.

Before explaining the embodiments of the invention in detail, it is to be understood that the invention is not limited in its application to the details of construction and the arrangement of components set forth in the following description and as illustrated in the drawings. The invention is capable of other embodiments and of being practiced and carried out in various ways. Also, it is to be understood that the phraseology and terminology used herein is for the purpose of description and should not be regarded as limiting.

DESCRIPTION OF THE PREFERRED EMBODIMENT

Figure 1:
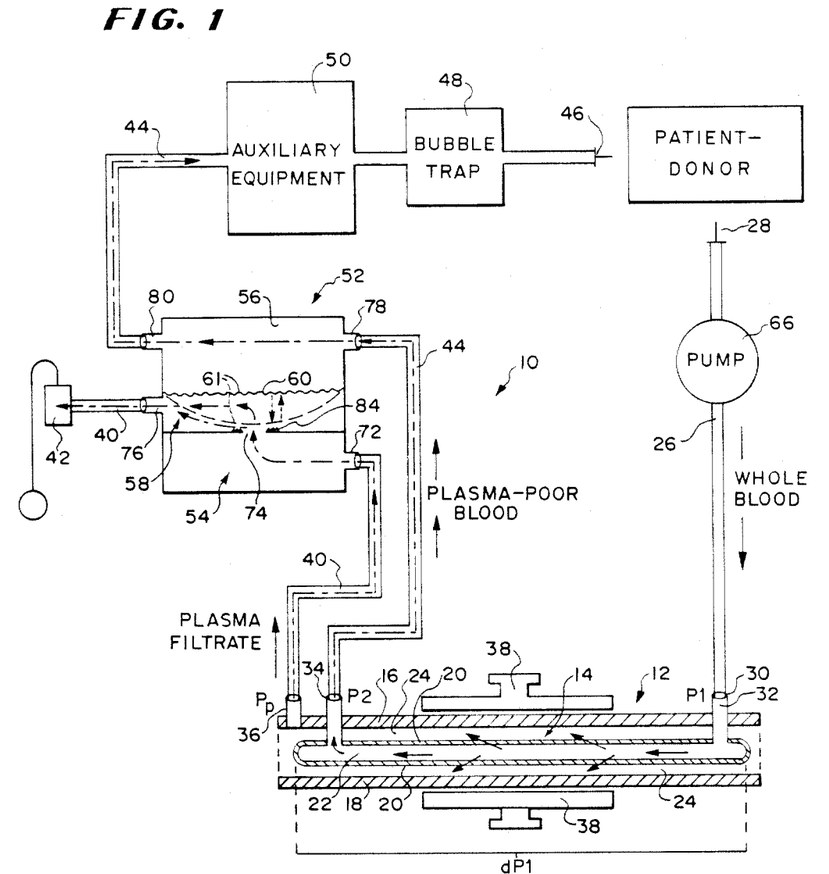
FIG. 1 is an essentially diagrammatic view of a membrane plasmapheresis apparatus which embodies various of the features of the invention and which utilizes a module in which spaced-apart sheets of microporous membranes are supported.

A membrane plasmapheresis apparatus 10 is shown in FIG. 1 which is operative for removing, or "harvesting", the plasma from whole blood for exchange, transfusion, or fractionation purposes.

The apparatus 10 includes a module or cell 12 in which microporous membranes 14 are housed. Various membranes 14 can be used, provided that they have a pore size suited for separating the plasma from whole blood, given the proper conditions of pressure and flow rates across the membrane surfaces.

The module 12 itself may also be variously constructed, according to the membrane configuration utilized. Two alternate embodiments are shown, respectively, in FIGS. 1 and 2. It should be appreciated, however, that numerous other embodiments are possible.

In the embodiment shown in FIG. 1, the module 12 includes first and second generally planar members, respectively 16 and 18, defining a housing in which two sheets of a microporous membrane 20 having a pore size of about 0.1 micron to 2 microns are positioned in a facing, spaced-apart relationship. A fluid path 22 is thus formed between the membranes 20, and the module 12 includes an inlet and outlet port, respectively 32 and 34, communicating at opposite ends of the fluid path 22. Open volumes 24 are also formed between the outer surfaces of the membranes 20 and the interior surfaces of the planar members 16 and 18, and the module 12 includes an outlet port 36 communicating with the volumes 24.

Figure 2:
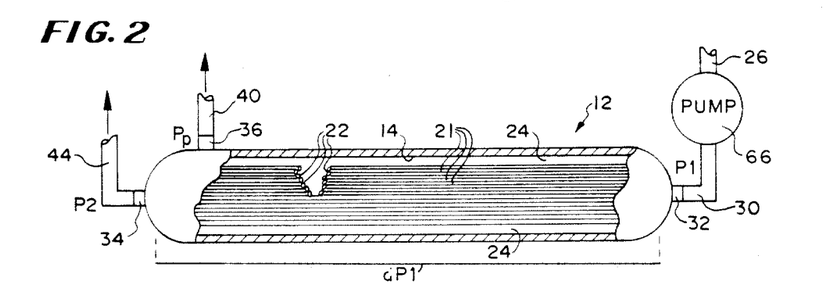
FIG. 2 is an essentially diagrammatic view of a module in which a cluster of hollow fiber membranes are supported and which is adapted for use with the membrane plasmapheresis apparatus shown in FIG. 1.

In the alternate embodiment shown in FIG. 2, the module 12 takes the form of a generally tubular housing in which a cluster of individual hollow fiber membranes 21 is supported. The hollow fiber membranes 21 can be fabricated from various materials, for example, polypropylene having a maximum pore size of about 0.6 microns and an average pore size in the neighborhood of 0.3 microns. The hollow bore of each fiber 21 defines the fluid path 22 corresponding to the one heretofore described with respect to the FIG. 1 embodiment. The tubular housing is constructed so as to form an open volume 24 circumferentially enveloping the hollow fiber cluster. As in the FIG. 1 embodiment, the module 12 includes inlet port 32 and outlet ports 34 and 36.

The apparatus 10 also includes a whole blood inlet conduit 26 having at one end thereof a phlebotomy needle 28 for insertion into the arm of a patient-donor. The other end 30 of the conduit 26 is attached to the inlet port 32 of the module 12.

The apparatus 10 further includes an in-line pump 66, for example, a peristaltic pump, which delivers whole blood from the patient-donor to the inlet port 32 of the module 12 subject to a predetermined inlet pressure which is under the control of the operator. The inlet pressure will hereafter be referred to and is shown in FIGS. 1 and 2 as P1.

As the whole blood traverses the length of the fluid pathway 22, a predetermined pressure drop occurs. This pressure drop is symbolized as dP1 in FIGS. 1 and 2. The size of the pressure drop dP1 depends principally upon the fluid volume of the pathway 22, which, in the FIG. 1 embodiment, depends in large part upon the lateral spacing between the sheet membranes 20. This lateral spacing is controlled by use of an adjustable clamp 38, which presses the planar members 16 and 18 together to achieve the desired pressure drop dP1.

In the FIG. 2 embodiment, the interior diameter of the hollow bore of each hollow fiber 21 is preselected to achieve the desired pressure drop, obviating the need for the clamp 38.

By carefully controlling the magnitudes of the inlet pressure P1 and the pressure drop dP1, the whole blood experiences a desired sheer rate as it traverses the membranes 20 or 21. This causes the red cells, leukocytes, and platelets to proceed in a laminar path across the membranes 20 or 21. At the same time, a determinable transmembrane pressure, or TMP, is generated, which, when within the operationally desirable limits of between approximately 50 mmHg to 100 mmHg, acts as a driving force to cause only the plasma to pass through the pores of the membranes 20 or 21 and into the volumes 24. However, as will be discussed in greater detail later herein, should the transmembrane pressure exceed a critical level (approximately 120 mmHg), hemolysis can occur.

To conduct the plasma filtrate from the module 12, the apparatus 10 includes a collection conduit 40 attached to the outlet port 36 in flow communication with the plasma filtrate volumes 24. The conduit 40 has an end connected to a plasma filtrate collection bag 42. Typically, this plasma filtrate is subject to a pressure (Pp in FIGS. 1 and 2) which is at or near atmospheric pressure, or ∅ mmHg.

To conduct the cellular components which do not pass through the membranes 20 or 21 from the module 12, these components now being collectively referred to as plasma-poor blood, the apparatus 10 includes a transfusion set 44 attached to the outlet port 34. The transfusion set 44 includes a phlebotomy needle 46 for insertion into the patient-donor to return the conducted plasma-poor blood to the patient-donor.

A bubble trap 48 is preferably connected in line with the transfusion set 44 between the outlet port 34 and the needle 46. Auxiliary equipment (generally designated by the numeral 50 in FIG. 1), such as a blood warmer, can also be connected in line with the transfusion set 44 to enhance the conduction of plasma-poor blood back to the patient-donor.

It has been observed that the presence of the various operationally necessary or desirable equipment positioned in the flow path of the plasma-poor blood downstream of the module 12 (i.e., the transfusion set 44, the needle 46, and any auxiliary equipment 50) collectively generates a resistance to the return of the plasma-poor blood. This resistance will hereafter be identified as the backside pressure (symbolized as P2 in FIGS. 1 and 2). Also contributing to the magnitude of the backside pressure P2 is the blood pressure of the individual patient-donor, as well as any random movement of patient-donor's arm during the procedure, which can cause a temporary occlusion in the flow path. The magnitude of the backside pressure P2 is often significant and can suddenly and randomly fluctuate during the course of the procedure between 20 mmHg and 150 mmHg.

It has also been observed that these sudden and random fluctuations in the backside pressure P2, if not compensated for, serve to induce correspondingly sudden and random variations in the transmembrane pressure of the apparatus 10. Thus, the presence of equipment downstream of the module 12 causes the transmembrane pressure to be unstable and can lead to sudden and random elevations of the transmembrane pressure above operationally desirable levels to a magnitude above 120 mmHg. At this critical level, the red cells traversing the membranes 20 or 21 can themselves be driven into the pores of the membranes 20 or 21 and be torn, damaged, or destroyed. Hemolysis results.

Efforts can be made to stabilize the transmembrane pressure at operationally desirable levels by removing as many of the sources of the backside pressure P2 as possible. For example, the size of the phlebotomy needle 46 can be enlarged (the smaller the needle, the larger the pressure developed, and vice versa), but this, in turn, can lead to patient-donor discomfort. Or, the use of ancillary equipment 50 downstream of the module 12 can be minimized, but such equipment is desirable for an efficient plasmapheresis procedure. To deal with the problem, the operator can also constantly adjust the elevation of the plasma collection bag 42, but such activitities divert operator attention from other necessary duties. In short, efforts such as those detailed run counter to patient-donor comfort and an efficient membrane plasmapheresis procedure and indeed do not and cannot completely stabilize the transmembrane pressure. The blood pressure of the particular patient-donor, or any arm movement of the patient-donor during the procedure, are variables which simply cannot be anticipated and instantly compensated for.

In order to effectively stabilize the transmembrane pressure at operationally desired levels, regardless of the presence of and fluctuations in the backside pressure P2, the apparatus 10 includes fluid flow control means 52. The control means 52 is operative for metering the flow of plasma filtrate exiting the volumes 24 in response to the then existent backside pressure P2 to maintain the pressure of the plasma filtrate (or Pp) at a magnitude equal to the magnitude of the then existent backside pressure P2.

Figure 3:
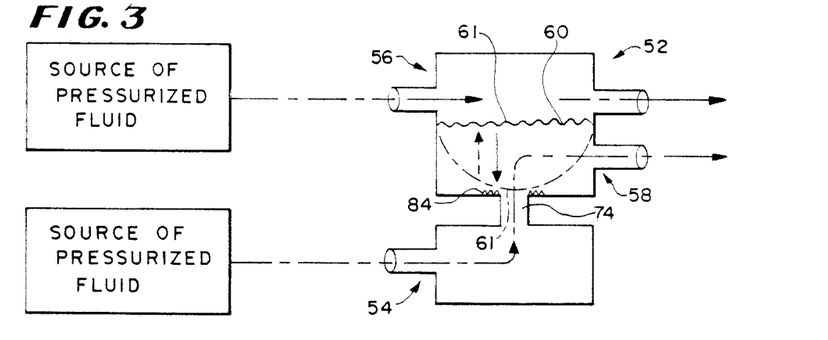
FIG. 3 is an enlarged, diagrammatic and section view of a fluid flow control device suited for use with the apparatus shown in FIG. 1.

The control means 52 can be variously constructed. In the illustrated embodiment, as shown in FIG. 3, the control means 52 includes conduit means defining first, second and third fluid pathways, respectively 54, 56, and 58. The first and second fluid pathways 54 and 56 are each individually adapted to communicate with its own source of pressurized fluid for conducting fluid from the respective source. The third fluid pathway 58 is in flow communication with the first fluid pathway 54 to conduct pressurized fluid therefrom.

In addition, the third fluid pathway 58 includes first wall means 60 which forms an interface with a portion of the second fluid pathway 56. The first wall means 60 is made of a flexible material and is operative for movement (as is generally shown by the use of arrows and phantom lines in FIG. 3) to meter the flow communication between the first and third fluid pathways 54 and 56.

More particularly, and still referring principally to FIG. 3, in response to an initial condition in which the fluid pressure in the second pathway 56 exceeds the fluid pressure in the first pathway 54, the first wall means 60 is moved in response to the pressure differential to restrict the flow of fluid between the first and third pathways 54 and 56. This serves to elevate the fluid pressure in the first pathway 54 until substantial equilibrium between the fluid pressures in the first and second pathways 54 and 56 occurs. Thereafter, the first wall means 60 is operative to maintain this condition of substantial equilibrium, notwithstanding any subsequent variations in the fluid pressure in the second pathway 56.

The control means 52 as heretofore generally described may be assembled in various ways. In the particular embodiment shown in FIGS. 4 through 6, the control means 52 comprises a compact housing 62 enclosing an interior area 64. The interior area 64 is itself compartmentalized by spaced wall means 66 into the three fluid pathways 54, 56, and 58 heretofore described.

Figure 5:
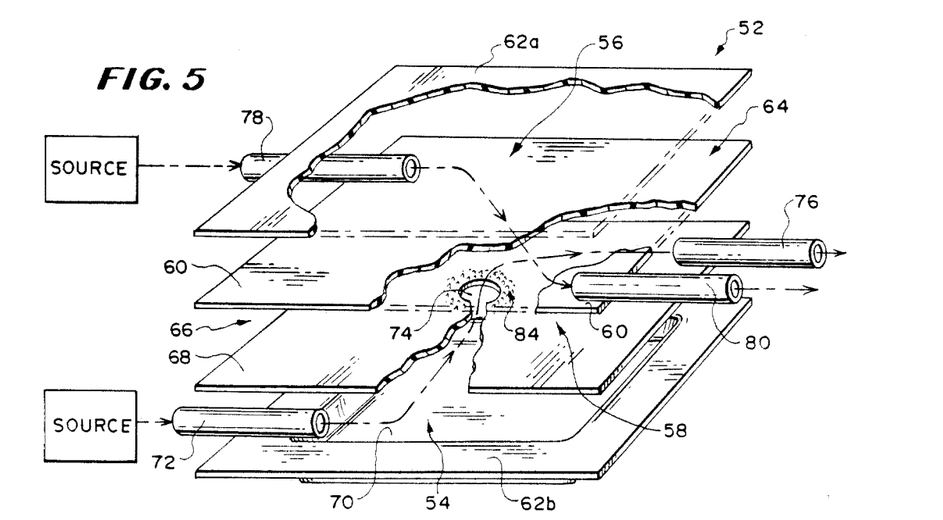
FIG. 5 is an exploded perspective view of the device shown in FIG. 4, with parts broken away to show the flow of fluids through the device.
Figure 6:
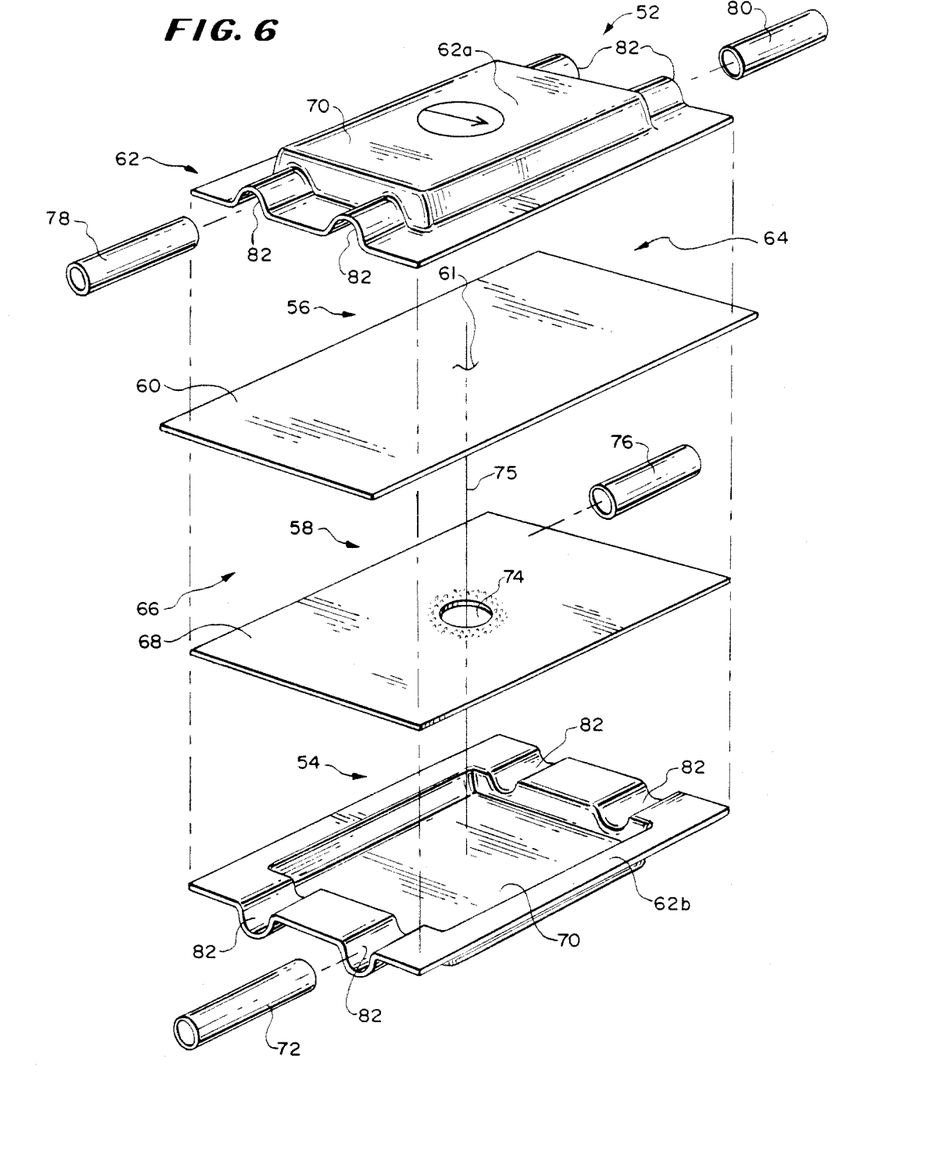
FIG. 6 is another exploded perspective view of the component parts of the device shown in FIG. 4.

More particularly, and as best seen in FIGS. 5 and 6, the wall means 66 includes the previously described first wall means 60 which forms the flexible interface between the second and third fluid pathways 56 and 58. The wall means 66 also includes second wall means 68, which forms an interface between the first and third fluid pathways 54 and 58.

In this arrangement, as can best be seen in FIG. 5, the three fluid pathways 54, 56, and 58 extend in a generally parallel and stacked relationship one above the other within the housing interior 64. The third fluid pathway 58 is positioned in this arrangement between the first and second pathways 54 and 56, which are themselves spaced at opposite ends of the interior area 38. By virtue of the raised exterior portions 70 of the housing 62, the enclosed portions of the first and second pathways 54 and 56 can be viewed as defining oppositely spaced chambers within the housing interior 64.

In this assemblage, the first pathway 54 includes an inlet portion 72 which extends outwardly of the housing 62 and which is adapted for communication with one source of pressurized fluid. The second wall means 68 is provided with an opening 74 which, in the illustrated embodiment, extends generally at a right angle to the fluid flow path through the first pathway 54 and which provides the heretofore described flow communication between the first and third fluid pathways 54 and 58. In this respect, the opening 74 serves as an outlet portion for the first fluid pathway 54 and an inlet portion for the third fluid pathway 58. The third fluid pathway 58 further includes an outlet portion 76 which extends outwardly of the housing 62 and which communicates with the atmosphere.

The second fluid pathway 56 includes spaced, generally coplanar inlet and outlet portions, respectively 78 and 80, both of which extend outwardly of the housing 62. The inlet portion 78 is adapted for communication with the other source of pressurized fluid, and the outlet portion 80 communicates with the atmosphere.

This compact structural arrangement lends itself to construction utilizing relatively few preformed parts. It also lends itself to construction utilizing only plastic materials and the like which have been approved for contact with human blood. As a result, the illustrated embodiment of the control means 52 can be manufactured in an efficient and economical manner and constitute an essentially disposable unit.

More particularly, in the illustrated embodiment (see FIG. 6), the housing 62 includes upper and lower housing portions, respectively 62a and 62b, which can be manufactured from a suitable plastic material, such as by the use of injection molding techniques. Preferably, the upper and lower housing portions 62a and 62b are generally rigid or semirigid in construction and include a spaced pair of outwardly bowed or convex grooves 82 formed at each opposite end.

The second wall means 68 constitutes a presized sheet of suitable generally flexible plastic material in which the opening 74 is centrally located. The first wall means 60 comprises a presized sheet of flexible plastic material, with a thickness of approximately 15 mils.

To form the desired compartmentalization within the housing 62 (and as best seen in FIG. 5), the inlet portion 72 of the first fluid pathway 54 comprises a presized section of plastic polyvinyl chloride tubing which is sandwiched between the lower housing portion 62b and the second wall means 68. The grooves 82 of the upper and lower housing portions 62a and 62b form a bushing to receive the inlet tubing portion 72 (see FIG. 4).

The inlet and outlet portions 78 and 80 of the second fluid pathway 56 likewise comprise identical presized sections of plastic polyvinyl chloride tubing positioned diagonally across from each other and sandwiched between the upper housing portion 62a and the flexible sheet comprising the first wall means 60. This diagonal relationship between the tubing portions 78 and 80 assures a uniform, laminar flow of fluid within the second fluid path 56.

As before, the grooves 82 of the upper and lower housing portions 62a and 62b together form bushings to receive the inlet and outlet tubing portions 78 and 80.

In similar fashion, the outlet portion 76 of the third fluid pathway 58 comprises a presized section of plastic polyvinyl chloride tubing which is positioned generally diagonally across from the inlet tubing portion 72 of the first fluid pathway 58 and there sandwiched between the first wall means 60 and the second wall means 68 within the bushing formed by the cooperating grooves 82. The diagonal relationship between the tubing portions 72 and 76 assures a uniform and laminar flow of fluid into and out of the first and third fluid pathways 54 and 58 through the interconnecting opening 74.

Figure 4:
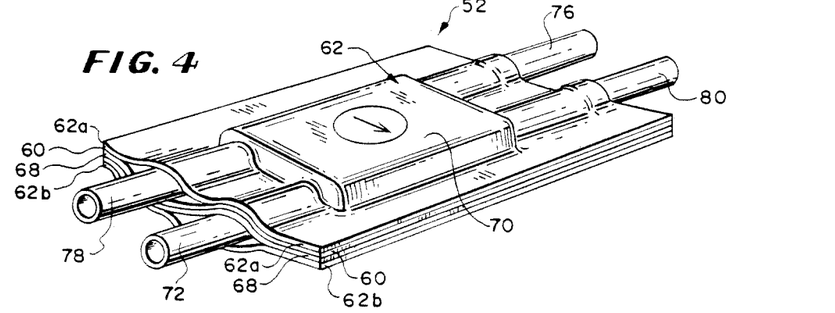
FIG. 4 is a perspective view of one structural embodiment of the pressurized fluid flow control device shown in FIG. 3.

The entire assembly shown in FIGS. 5 and 6 is sandwiched together into the compact configuration shown in FIG. 4 and peripherally sealed, such as by the use of radio frequency, heat, or solvent sealing methods. During such manufacture, the peripheries of the flexible first and second wall means 60 and 68 will conform to sealingly surround the adjacent tubing portions.

As can be best seen in FIGS. 5 and 6, the flexible first wall means 60 is generally oppositely spaced in facing relationship from the opening 74 formed in the second wall means 68. Furthermore, the axis 75 of the opening 74 (see FIG. 6) is generally aligned with the midportion 61 of the first wall means 60. Because of this construction, coupled with the inherent flexibility of the first wall means 60, the first wall means 60 is operative for movement in response to fluid pressures in a path along the axis 75 toward and away from the opening 74.

While the control means 52 of the above described construction can be of various sizes, in one operative embodiment thereof, the housing 62 is approximately 2.5 inches in overall length (exclusive of the outwardly extending tubings), approximately 1.5 inches in overall width, and approximately 0.5 inches in overall thickness.

Referring now back to FIG. 1, the control means 52 is connected downstream of the module 12 in flow communication with both the transfusion set 44 and the plasma collection conduit 40. More particularly, the inlet portion 72 of the first fluid pathway 54 is attached in flow communication with the outlet port 36, and the outlet portion 76 of the third fluid pathway 58 is attached in flow communication with the plasma collection container 42.

As a result of this interconnection in line with the collection conduit 40, plasma filtrate flows out of the plasma volumes 24, subject to the plasma pressure Pp, into and through the first and third fluid pathways 54 and 58 via the opening 74, and thence toward the plasma collection container 42.

The inlet and outlet portions 78 and 80 of the second fluid pathway 56 are connected in line with transfusion set 44 upstream of the bubble trap 48 and any associated auxiliary equipment 50.

As a result of this in line connection, the plasma-poor blood flows from the outlet port 70 subject to the back pressure P2, into and through the laminar flow path of the second fluid pathway 56, and thence toward the downstream equipment. The laminar flow path provided by the second fluid pathway 56 minimizes undesirable mixing, or turbulence, of the plasma-poor blood during its return to the patient-donor. This, in turn, reduces the chance of hemolysis which can be occasioned by such mixing.

At the outset of the plasmapheresis procedure, a pressure differential will always exist between the plasma pressure Pp (typically at 0 mmHg) and the backside blood pressure P2 (typically between 20 mmHg and 150 mmHg). Assuming that the flexible first wall means 60 is disposed in an initial position (shown in solid lines in FIGS. 1 and 3) which is generally parallel with the second wall means 68, the flexible first wall means 60 will respond to the pressure differential by moving in its axial path toward the opening 74. This is generally shown by arrows and in phantom lines in FIGS. 1 and 3.

This movement of the flexible wall means 60 toward the opening 74 will result in a change in the configuration of the flexible first wall means 60 from its essentially planar initial position (shown in solid lines in FIGS. 1 and 3) toward a generally convex configuration outwardly bowed into the third fluid pathway 32 (shown in phantom lines in FIGS. 1 and 3).

Closer proximity of the flexible first wall means 60, and, in particular, its midportion 61, to the opening 74 serves to restrict the flow of plasma filtrate through the opening 74. This restriction, in turn, causes the plasma fluid pressure Pp in the first pathway 54 to rise. This plasma pressure elevation will proceed until pressure equalization with the then existent backside fluid pressure P2 in the second pathway 56 occurs.

It should be appreciated that the particular configuration the flexible wall means 60 will assume within the third pathway 58 and relative to the opening 74 to meter the flow of plasma filtrate and bring about pressure equalization will depend upon the particular magnitudes of the then prevailing plasma filtrate and plasma-poor blood pressures Pp and P2, as well as the then prevailing fluid flow rates.

Should the backside pressure P2 in the second pathway 56 subsequently increase or decrease, the flexible wall means 60 will correspondingly change its configuration by moving in its axial path toward a new position, respectively, closer to or farther away from the opening 74. This automatically changes the previously imposed restriction to the flow of plasma filtrate in lieu of a new restriction. The flow of plasma filtrate will be metered at the new rate until the plasma filtrate pressure Pp achieves equalization with the higher or lower backside pressure P2.

In reality, the flexible first wall means 60 is thus movable in its axial path through a range of positions which are progressively spaced closer to or farther away from the opening 74. The particular position and configuration of the flexible wall means 60 within this range will depend upon the particular fluid pressures and flow rates then prevailing.

It should be appreciated that the movement of the flexible wall means 60 as just described occurs virtually instantaneously with fluctuations in the backside pressure P2. Thus, the control means 52 is operative to continuously maintain pressure equilibrium between the plasma filtrate pressure Pp and the backside pressure P2.

It should also be appreciated that the control means 52 as heretofore described preferably operates without the use of valve seats or the like. Thus, the movement of the flexible wall means 60 toward the opening 74 will not normally serve to completely close or seal the opening 74, and thereby completely block flow communication therethrough.

Furthermore, in the illustrated and preferred embodiment, the area 84 circumferentially surrounding the opening 74 is roughened or contoured to break any surface tension that might develop between the area 84 and the flexible wall means 60. This further assures that the flexible wall means 60 will not assume a position completely blocking the opening 74, thereby assuring a desirable constant and continuous flow of plasma filtrate in the apparatus 10.

The plasmapheresis apparatus 10 as above described has been observed to continuously meter the conduction of plasma filtrate in response to the plasma-poor, or backside, blood pressure P2 to maintain substantial equilibrium between the pressure of the plasma filtrate (Pp) and the backside pressure P2.

The resulting transmembrane pressure of the apparatus 10 has been observed to be essentially stable, regardless of the magnitude of the then existent backside pressure P2, at a magnitude which represents only the flow resistance of the module 12 itself (or P1−dP1), which is a quantity under direct operator control. In particular, when an inlet pressure P1 of between 150 mmHg and 200 mmHg is maintained, along with a constantly maintained pressure drop Dpl across the module 12 of approximately 100 mmHg, the apparatus 10 serves to stabilize the transmembrane pressure within the operationally desirable range of between 50 mmHg and 100 mmHg, even though the backside pressure P2 may at the same time be undergoing random fluctuations of between 20 mmHg and 150 mmHg.

In addition, the apparatus 10 has been observed to continuously maintain an uninterrupted flow of plasma filtrate from the module 12 and through the first and third pathways 54 and 58 at a rate of between 10 cubic centimeters per minute and 80 cubic centimeters per minute. At the same time, the apparatus 10 has been observed to continuously maintain an uninterrupted flow of plasma-poor blood from the module 12 and through the second pathway 56 at a rate of between 40 cubic centimeters per minute and 300 cubic centimeters per minute.

The apparatus 10 also permits the use of operationally desirable components of membrane plasmapheresis, such as a smaller, more comfortable needle, and auxiliary equipment such as the blood warmer, without effecting the stability of the transmembrane pressure and without causing hemolysis.

It should be appreciated that various changes and modifications can be made without departing from the spirit of the invention or from the scope of the appended claims.

We claim:

1. A membrane plasmapheresis process which comprises the steps of introducing a flow of whole blood subject to a predetermined inlet pressure into a fluid path defined by membrane fluid path means, across a membrane, the membrane having a pore size suited for filtering plasma from the whole blood, conducting plasma-poor blood from the defined membrane fluid path through a plasma-poor blood fluid path defined by plasma-poor blood fluid path means, subject to a plasma-poor blood pressure which is subject to random variations, conducting plasma filtrate from the defined membrane fluid path through a filtrate fluid path defined by filtrate-fluid path means, subject to a plasma filtrate pressure which is initially less than the plasma-poor blood pressure, diverting the plasma filtrate in the defined filtrate fluid path through an intermediate fluid pathway defined by intermediate fluid pathway means, the defined intermediate fluid pathway having a filtrate inlet defined by filtrate inlet means, said filtrate inlet means further defining a filtrate inlet axis such that the plasma filtrate enters the defined intermediate fluid pathway from the defined filtrate fluid path through the defined filtrate inlet generally along the defined axis thereof, and a filtrate outlet defined by filtrate outlet means, through which the plasma filtrate exits the defined intermediate fluid pathway and returns to the defined filtrate fluid path, and variably restricting flow of plasma filtrate through the defined filtrate inlet by placing between the defined plasma-poor blood fluid path and the defined intermediate fluid pathway a flexible wall means generally oppositely spaced from and in facing relationship to the defined filtrate inlet, the flexible wall means moving in response to a pressure differential between the plasma-poor blood and the plasma filtrate, toward and away from the defined filtrate inlet in a path defined generally along the defined axis of the defined filtrate inlet to establish and thereafter maintain substantial equilibrium between the pressure of the plasma filtrate and the pressure of the plasma-poor blood, despite random variations in the plasma-poor blood pressure.

2. A process according to claim 1 and further including the step of maintaining an uninterrupted flow of plasma filtrate through the defined filtrate inlet while the flow is being variably restricted.

3. A process according to claim 1 or 2 and further including the step of maintaining a laminar flow of plasma-poor blood along one side of the flexible wall means.

4. A process according to claim 3 and further including the step of maintaining an uninterrupted flow of plasma-poor blood along one side of the flexible wall means.

5. A membrane phasmapheresis apparatus comprising:
   membrane means for filtering plasma from whole blood,
   means for forming a fluid path across said membrane means,
   means communicating with said membrane means for communication with a source of whole blood for introducing the whole blood subject to a predetermined inlet pressure into the membrane fluid path defined by said membrane fluid path forming means, to filter the plasma from the whole blood,
   means communicating with said membrane means for conducting plasma-poor blood from the defined membrane fluid path subject to a plasma-poor blood pressure which is subject to random variations,
   means communicating with said membrane means for conducting plasma filtrate from the defined membrane fluid path subject to a plasma filtrate pressure which is initially less than the plasma-poor blood pressure,
   means for forming in said plasma filtrate conduction means an intermediate fluid pathway, a filtrate inlet to the defined intermediate fluid pathway and a filtrate inlet axis to the defined filtrate inlet such that the plasma filtrate is conducted from said plasma filtrate conduction means into the defined intermeidate fluid pathway through the defined filtrate inlet generally along the defined axis thereof, and means for forming a filtrate outlet, through which the plasma filtrate is conducted out of the defined intermediate fluid pathway and back to said plasma filtrate conduction means, and
   means forming between a portion of said plasma-poor blood conduction means and the defined intermediate fluid pathway a flexible wall generally oppositely spaced from and in facing relationship to the defined filtrate inlet, said flexible wall means being operatively movable in response to the pressure differential between the plasma-poor blood and the plasma filtrate, toward and away from the defined filtrate inlet in a path defined generally along the defined axis of the defined filtrate inlet for variably restricting the conduction of plasma filtrate through the defined filtrate inlet to establish and thereafter maintain substantial equilibrium between the pressure of the plasma filtrate and the pressure of the plasma-poor blood, despite random variations in the plasma-poor blood pressure.

6. A membrane plasmapheresis apparatus according to claim 5 and further including means for maintaining an uninterrupted flow of plasma filtrate through the defined filtrate inlet into the defined intermediate fluid pathway during movement of said flexible wall means.

7. A membrane plasmapheresis apparatus according to claim 5 or 6 and further including means for maintaining a laminar flow of plasma-blood along one side of said flexible wall means.

8. A membrane plasmapheresis apparatus according to claim 7 and further including means for maintaining an uninterrupted flow of plasma-poor blood along one side of said flexible wall means.

9. The process according to claim 1, including placing the flexible wall means such that it has an initial position generally perpendicular to the defined axis of the defined filtrate inlet.

10. A membrane plasmapheresis process which comprises the steps of
    introducing a flow of whole blood subject to a predetermined inlet pressure into a fluid path defined by membrane fluid path means, across a membrane, the membrane having a pore size suited for filtering plasma from the whole blood,
    conducting plasma-poor blood from the defined membrane fluid path through a plasma-poor blood fluid path defined by plasma-poor blood fluid path means, subject to a plasma-poor blood pressure which is subject to random variations,
    conducting plasma filtrate from the defined membrane fluid path through a filtrate fluid path defined by filtrate-fluid path means, subject to a plasma filtrate pressure which is initially less than the plasma-poor blood pressure,
    diverting the plasma filtrate in the defined filtrate fluid path through an intermediate fluid pathway defined by intermediate fluid pathway means, the defined intermediate fluid pathway having a filtrate inlet defined by filtrate inlet means, said filtrate inlet means further defining a filtrate inlet axis, such that the plasma filtrate enters the defined intermediate fluid pathway from the defined filtrate fluid path through the defined filtrate inlet generally the defined axis thereof, and a filtrate outlet defined by filtrate outlet means, through which the plasma filtrate exits the defined intermediate fluid pathway and returns to the defined filtrate fluid path, and
    variably restricting flow of plasma filtrate through the defined filtrate inlet by placing between the defined plasma-poor blood fluid path and the defined intermediate fluid pathway a flexible wall means such that the wall means has an initial position generally perpendicular to the defined axis of the defined filtrate inlet, the flexible wall means moving in response to a pressure differential between the plasma-poor blood and the plasma filtrate, toward and away from the defined filtrate inlet in a path defined generally along the defined axis of the devined filtrate inlet to establish and thereafter maintain substantial equilibrium between the pressure of the plasma filtrate and the pressure of the plasma-poor blood, despite random variations in the plasma-poor blood pressure.

11. The process according to claim 10, including placing the flexible wall means generally oppositely spaced from and in facing relationship to the defined filtrate inlet.

12. The process accordiing to claims 1 or 10, wherein the flexible wall means includes a mid portion, further including aligning the defined filtrate inlet axis with the mid portion of the flexible wall means.

13. A membrane plasmapheresis process which comprises the steps of introducing a flow of whole blood subject to a predetermined inlet pressure into a fluid path defined by membrane fluid path means, across a membrane, the membrane having a pore size suited for filtering plasma from the whole blood, conducting plasma-poor blood from the defined membrane fluid path through a plasma-poor blood fluid path defined by plasma-poor blood fluid path means, subject to a plasma-poor blood pressure which is subject to random variations, conducting plasma filtrate from the defined membrane fluid path through a filtrate fluid path defined by filtrate-fluid path means, subject to a plasma filtrate pressure which is initially less than the plasma-poor blood pressure, diverting the plasma filtrate in the defined filtrate fluid path through an intermediate fluid pathway defined by intermediate fluid pathway means, the defined intermeidate fluid pathway having a filtrate inlet defined by filtrate inlet means, through which the plasma filtrate enters the defined intermediate fluid pathway from the defined filtrate fluid path, and a filtrate outlet defined by filtrate outlet means, through which the plasma filtrate exits the defined intermediate fluid pathway and returns to the defined filtrate fluid path, and placing between the defined plasma-poor blood fluid path and the defined intermediate fluid pathway a flexible wall means, said flexible wall means moving in response to a pressure differential between the plasma-poor blood and the plasma filtrate to establish and thereafter maintain substantial equilibrium between the pressure of the plasma filtrate and the pressure of the plasma-poor blood, despite random variations in the plasma-poor blood pressure.

14. The process according to claim 13, wherein the flexible wall means includes a mid portion and wherein the defined filtrate inlet has an axis therethrough defined by said filtrate inlet means, further including aligning the defined filtrate inlet axis with the mid portion of the flexible wall means.

15. The apparatus according to claim 5, further wherein said flexible wall means is disposed in an initial position that is generally perpendicular to the defined axis of the defined filtrate inlet.

16. A membrane plasmapheresis apparatus comprising:

membrane means for filtering plasma from whole blood, means for forming a fluid path across said membrane means, means communicating with said membrane means for communication with a source of whole blood for introducing the whole blood subject to a predetermined inlet pressure into the membrane fluid path defined by said membrane fluid path forming means, to filter the plasma from the whole blood, means communicating with said membrane means for conducting plasma-poor blood from the defined membrane fluid path subject to a plasma-poor blood pressure which is subject to random variations, means communicating with said membrane means for conducting plasma filtrate from the defined membrane fluid path subject to a plasma filtrate pressure which is initially less than the plasma-poor blood pressure, means for forming in said plasma filtrate conduction means an intermediate fluid pathway, a filtrate inlet to the defined intermediate fluid pathway and a filtrate inlet axis to the defined filtrate inlet such that plasma filtrate is conducted from said plasma filtrate conduction means into the defined intermediate fluid pathway through the defined filtrate inlet generally along the defined axis thereof, and means for forming a filtrate outlet, through which the plasma filtrate is conducted out of the defined intermediate fluid pathway and back to said plasma filtrate conduction means, and means forming between a portion of said plasma-poor blood conduction means and the defined intermediate fluid pathway a flexible wall disposed in an initial position generally perpendicular to the defined axis of the defined filtrate inlet, said flexible wall means moving in response to the pressure differential between the plasma-poor blood and the plasma filtrate, toward and away from the defined filtrate inlet in a path defined generally along the defined axis of the defined filtrate inlet for variably restricting the conduction of plasma filtrate through the defined filtrate inlet to establish and thereafter maintain substantial equilibrium between the pressure of the plasma filtrate and the pressure of the plasma-poor blood, despite random variations in the plasma-poor blood pressure.

17. The apparatus according to claim 16, further wherein said flexible wall means is generally oppositely spaced from and in facing relationship to the defined filtrate inlet.

18. The apparatus according to claims 5 or 16, further including a mid portion of said flexible wall means, said mid portion being aligned with the defined filtrate inlet axis.

19. A membrane plasmapheresis apparatus comprising:

membrane means for filtering plasma from whole blood, means for forming a fluid path across said membrane means, means communicating with said membrane means for communication with a source of whole blood for introducing the whole blood subject to a predetermined inlet pressure into the membrane fluid path defined by said membrane fluid path forming means, to filter the plasma from the whole blood, means communicating with said membrane means for conducting plasma-poor blood from the defined membrane fluid path subject to a plasma-poor blood pressure which is subject to random variations, means communicating with said membrane means for conducting plasma filtrate from the defined membrane fluid path subject to a plasma filtrate pressure which is initially less than the plasma-poor blood pressure, means for forming in said plasma filtrate conduction means an intermediate fluid pathway, and a filtrate inlet to the defined intermediate fluid pathway, through which the plasma filtrate is conducted from said plasma filtrate conduction means into the defined intermediate fluid pathway, and a filtrate outlet defined by filtrate outlet means, through which the plasma filtrate is conducted out of said defined intermediate fluid pathway and back to said plasma filtrate conduction means, and means forming between a portion of said plasma-poor blood conduction means and said defined intermediate fluid pathway a flexible wall moving in response to the pressure differential between the plasma-poor blood and the plasma filtrate to establish and thereafter maintain substantial equilibrium bewtween the pressure of the plasma filtrate and the pressure of the plasma-poor blood, despite random variations in the plasma-poor blood pressure.

20. The apparatus according to claim 19, further including a mid portion of said flexible wall means, the defined filtrate inlet having an axis therethrough defined by said filtrate inlet means, said mid portion being aligned with the defined filtrate inlet axis.

* * * * *